(12) United States Patent
Shimamoto (10) Patent No.: US 7,670,784 B2
(45) Date of Patent: Mar. 2, 2010

(54) β-BENZYLOXYASPARTIC ACID DERIVATIVES HAVING TWO SUBSTITUENTS ON THEIR BENZENE RINGS (75) Inventor: Keiko Shimamoto, Suita (JP)

(73) Assignee: Suntory Holdings Limited, Osaka (JP)

(*) Notice: Subject to any disclaimer, the term of this patent is extended or adjusted under 35 U.S.C. 154(b) by 287 days.

(21) Appl. No.: 11/794,124

(22) PCT Filed: Dec. 26, 2005

(86) PCT No.: PCT/JP2005/023773

§ 371 (c)(1),
(2), (4) Date: Jun. 26, 2007

(87) PCT Pub. No.: WO2006/070737

PCT Pub. Date: Jul. 6, 2006

(65) Prior Publication Data

US 2008/0070321 A1    Mar. 20, 2008

(30) Foreign Application Priority Data

Dec. 27, 2004    (JP) .............................. 2004-377557

(51) Int. Cl.
G01N 33/53    (2006.01)
G01N 33/566    (2006.01)
C07K 1/14    (2006.01)
C07C 229/24    (2006.01)

(52) U.S. Cl. .................... 435/7.1; 435/7.8; 435/7.92; 436/501; 530/413; 562/452

(58) Field of Classification Search .................... None
See application file for complete search history.

(56) References Cited

FOREIGN PATENT DOCUMENTS

WO    03/000698    1/2003
WO    2005/090268    9/2005

OTHER PUBLICATIONS

David Nicholls et al., "The Release And Uptake Of Excitatory Amino Acids", TIPS Special Report 1991, pp. 68-74, Elsevier Science Publishers Ltd., 1990.

(Continued)

*Primary Examiner*—Shafiqul Haq
(74) *Attorney, Agent, or Firm*—Drinker Biddle & Reath LLP (57) ABSTRACT

The present invention provides a β-benzyloxyaspartic acid derivative having two substituents on its benzene ring, wherein the derivative has L-glutamate uptake inhibitory effect. More specifically, the present invention provides a compound of Formula (1) having an inhibitory effect against the glutamate uptake activity of L-glutamate transporters (wherein $R^1$ represents an optionally substituted aromatic group, and substituent $R^2$ represents a group selected from an optionally substituted linear or branched $C_1$-$C_{30}$ aliphatic group whose chain may contain nitrogen or oxygen, and an optionally substituted aromatic group) or a salt thereof, and a method for obtaining the above compound, as well as a method for purifying or detecting L-glutamate transporters using the above compound.

14 Claims, 3 Drawing Sheets

OTHER PUBLICATIONS

Jeffrey D. Rothstein et al., "Decreased Glutamate Transport By The Brain And Spinal Cord in Amyotrophic Lateral Sclerosis", The New England Journal Of Medicine, May 28, 1992, pp. 1464-1468.

Bruno Lebrun et al., "New β-Hydroxyaspartate Derivatives Are Competitive Blockers For The Bovine Glutamate/Aspartate Transporter", The Journal of Biological Chemistry, vol. 272, No. 33, Aug. 15, 1997, pp. 20336-20339, The American Society For Biochemistry and Molecular Biology, Inc., USA.

Keiko Shimamoto et al., "DL-*threo*-β-Benzyloxyaspartate, A Potent Blocker Of Excitatory Amino Acid Transporters", Molecular Pharmacology, vol. 53, 1998, pp. 195-201, The American Society For Pharmacology And Experimental Therapeutics.

Yasushi Shigeri et al., "Effects of *threo*-β-Hydroxyaspartate Derivatives On Excitatory Amino Acid Transporters (EAAT4 and EAAT5)", Journal of Neurochemistry, 2001, vol. 79, pp. 297-302.

Jean-Yves Chatton et al.,"Effects of Glial Glutamate Transporter Inhibitors On Intracellular $Na^+$ in Mouse Astrocytes", Brain Research, 2001, vol. 893, pp. 46-52.

Keiko Shimamoto et al., "Characterization of Novel L-*threo*-β-Benzyloxyaspartate Derivatives, Potent Blockers Of The Glutamate Transporters", Molecular Pharmacology, 2004, vol. 65, No. 4, pp. 1008-1015, The American Society For Pharmacology And Experimental Therapeutics.

International Search Report dated Feb. 21, 2006 in International PCT Application No. PCT/JP2005/023773.

β-BENZYLOXYASPARTIC ACID DERIVATIVES HAVING TWO SUBSTITUENTS ON THEIR BENZENE RINGS

CROSS REFERENCE TO RELATED APPLICATIONS

This application is the National Stage of International Application No. PCT/JP2005/023773, filed Dec. 26, 2005, and claims benefit of Japanese Application No. 2004-377557, filed Dec. 27, 2004, both of which are herein incorporated by reference in their entirety.

TECHNICAL FIELD

The present invention relates to a β-benzyloxyaspartic acid derivative having two substituents on its benzene ring, wherein the derivative has L-glutamate uptake inhibitory effect. More specifically, the present invention relates to a compound of Formula (1) having an inhibitory effect against the glutamate uptake activity of L-glutamate transporters (wherein $R^1$ represents an optionally substituted aromatic group, and substituent $R^2$ represents a group selected from an optionally substituted linear or branched $C_1$-$C_{30}$ aliphatic group whose chain may contain nitrogen or oxygen, and an optionally substituted aromatic group) or a salt thereof, and a method for obtaining the above compound, as well as a method for purifying or detecting L-glutamate transporters using the above compound.

BACKGROUND ART

L-Glutamate has been known as an excitatory neurotransmitter in the mammalian central nervous system, which not only induces rapid neurotransmission between synapses, but also participates in high-order and complex physiological processes such as memory and/or learning. Excitatory neurotransmission between synapses begins with release of glutamate from presynapses and ends with rapid uptake of glutamate from synaptic clefts by the action of high-affinity glutamate transporters present in nerve endings and glial cells (Attwell, D. and Nicholls, D., TIPS 68-74, 1991).

In certain genetic neurodegenerative diseases, a decrease in sodium-dependent glutamate uptake activity has been reported in the brains of some patients (Rothstein, J. D. et al., N. Eng. J. Med 326, 1464-1468, 1992). This directs attention to the expression and inhibition of glutamate transporter functions in connection with these diseases.

Under these circumstances, there is a demand for the development of transporter-specific inhibitors, particularly those acting as blockers, in order to elucidate transport mechanisms of glutamate transporters and to study relations between glutamate transporters and neurodegenerative diseases such as neuropathies including epilepsy, Huntington's disease, amyotrophic lateral sclerosis (ALS) and Alzheimer's disease.

The inventor of the present invention has already reported that β-hydroxyaspartic acid derivatives having a substituent at the β-position exhibit uptake inhibitory effect against all of the subtypes EAAT1 to EAAT5 (Lebrun, B. et al., J. Biol. Chem. 272, 20336-20339, 1997; Shimamoto, K. et al., Mol. Pharmacol. 53, 195-201, 1998; Shigeri, Y. et al., J. Neurochem, 79, 1207-1216, 2001). The inventor has found that especially compounds having a bulky substituent at the β-position act as blockers in all the subtypes and inhibit not only glutamate uptake, but also heteroexchange-induced glutamate leakage or sodium ion influx (Chatton, J-Y. et al., Brain Res. 893, 46-52, 2001). In particular, L-threo-β-benzyloxyaspartic acid (L-TBOA) shown in Formula (2) has a potent blocker effect, but has a lower affinity for glutamate receptors than existing inhibitors. For this reason, this compound has come to be used as a standard substance in glutamate transporter studies.

[Formula 1]

Formula (2)

The inventor has further found that compounds having an amino substituent at the meta-position of the benzyl group in L-TBOA show potent activity, and also have reported that especially benzoylamide compounds substituted at the para-position have high affinity (Shimamoto, K. et al., Mol. Pharmacol. 65, 1008-1015, 2004). Above all, the compound having a trifluoromethylbenzoyl group (TFB-TBOA) shown in Formula (3) was found to have an $IC_{50}$ value for uptake inhibitory activity being in the order of nM.

[Formula 2]

Formula (3)

On the other hand, protein purification is necessary to elucidate the three-dimensional structure of glutamate transporters to thereby clarify their substrate transport mechanisms and/or substrate binding sites. Affinity column chromatograph is an effective means for protein purification. Some attempts have been made to use antibodies for protein purification, but such attempts were disadvantageous in that proteins would lose their inherent functions during elution because of too strong a binding between antibody and protein. If a blocker can be used as a column ligand, elution under mild conditions will be permitted. For this reason, there has been a demand for a blocker that has a substituent capable of binding to an affinity column while showing potent L-glutamate uptake inhibitory activity. Among the above substituted TBOAs previously developed, those having an amino acid or biotin as a substituent can be expected to act as affinity column ligands, but their affinity was not sufficient (in the order of μM). Moreover, additional means have also been required to detect purified proteins.

DISCLOSURE OF THE INVENTION

The present invention provides a compound that has high inhibitory activity against glutamate uptake by L-glutamate transporters and that further acts as an affinity column ligand.

The present invention also provides a method for obtaining the above compound, and methods for purifying and detecting L-glutamate transporters using the above compound.

With focus on strong affinity of TFB-TBOA and its analogs, the inventor of the present invention has synthesized derivatives of TFB-TBOA and its analogs, which are modified to have an additional substituent, and have attempted to use these derivatives for the purpose of being held on a column carrier or of detection. As a result of extensive and intensive efforts, the inventor has found that a (2S,3S)-3-(3,5-diaminobenzyloxy)aspartic acid derivative of Formula (1) allows having of a substituent capable of binding to an affinity column while showing potent L-glutamate uptake inhibitory activity. This finding led to the completion of the present invention.

[Formula 3]

Namely, the present invention provides a compound of Formula (1) which allows having of a substituent capable of binding to an affinity column while showing potent L-glutamate uptake inhibitory activity (wherein $R^1$ represents an optionally substituted aromatic group, and substituent $R^2$ represents a group selected from an optionally substituted linear or branched $C_1$-$C_{30}$ aliphatic group whose chain may contain nitrogen or oxygen, and an optionally substituted aromatic group) or a salt thereof.

EMBODIMENT FOR CARRYING OUT THE INVENTION

Compound of Formula (1)

A compound of Formula (1) is a compound which allows having of a substituent capable of binding to an affinity column while showing potent L-glutamate uptake inhibitory activity, wherein $R^1$ represents an optionally substituted aromatic group, and substituent $R^2$ represents a group selected from an optionally substituted linear or branched $C_1$-$C_{30}$ aliphatic group whose chain may contain nitrogen or oxygen, and an optionally substituted aromatic group.

As defined above, the substituent $R^1$ is an optionally substituted aromatic group. Examples of the aromatic group represented by $R^1$ include a phenyl group, a naphthyl group and a pyridyl group, each of which may have a substituent on the aromatic ring. Examples of a substituent on the aromatic ring include a linear or branched $C_1$-$C_7$ alkyl group, a $C_4$-$C_{10}$ aryl group, a $C_1$-$C_6$ alkoxyl group, a nitro group, a cyano group, an amino group, a $C_1$-$C_7$ acylamino group, a carboxyl group, a halogen, a halogenated $C_1$-$C_6$ alkyl group, an azido group, and a 4-(3-(trifluoromethyl)-3H-diazirin-3-yl) group. Among them, a phenyl group substituted at the para-position has high L-glutamate inhibitory activity, and examples of such a substituent include a 4-(trifluoromethyl)phenyl group, a 4-ethylphenyl group, a 4-methoxyphenyl group, a 4-azidophenyl group, and a 4-(3-(trifluoromethyl)-3H-diazirin-3-yl)phenyl group.

As defined above, the substituent $R^2$ represents a group selected from an optionally substituted linear or branched $C_1$-$C_{30}$ aliphatic group whose chain may contain nitrogen or oxygen, and an optionally substituted aromatic group. Examples of a linear or branched $C_1$-$C_{30}$ aliphatic group include a methyl group, an ethyl group, a n-propyl group, an isopropyl group, a t-butyl group, a vinyl group, and a propenyl group. Such a linear or branched $C_1$-$C_{30}$ aliphatic group may contain nitrogen or oxygen within its chain, preferably 1 to 3 atoms for nitrogen and 1 to 8 atoms for oxygen. These aliphatic groups may also have an unsaturated bond or a substituent, and examples of a substituent for this purpose include an oxo group, a hydroxy group, a thiol group, an amino group, and a carboxyl group.

The moiety defined as $R^2CO$ includes groups derived from an amino acid, a peptide and polyethylene glycol, as exemplified by a glycyl group, an alanyl group, a β-alanyl group, a cysteinyl group, a 6-aminohexanoyl group, and peptides in which 2 to 5 of these groups are condensed. Further examples include a polyethylene glycol derivative represented by $H_2N$—$(CH_2CH_2O)_n$—$CH_2CO$ (n=2-6), as well as a linear compound prepared by condensation between this derivative and an amino acid or peptide.

Examples of the aromatic group defined for the substituent $R^2$ include a phenyl group, a naphthyl group and a pyridyl group, each of which may have a substituent on the aromatic ring. Examples of a substituent on the aromatic ring include a linear or branched $C_1$-$C_7$ alkyl group, a $C_4$-$C_{10}$ aryl group, a $C_1$-$C_6$ alkoxyl group, a $C_1$-$C_7$ acylamino group, a halogen, and a halogenated $C_1$-$C_6$ alkyl group.

When a linker having an amino group is used as substituent $R^2$, its free amino group can be easily bound to carboxylic acid or an active ester of carboxylic acid or a halogenated alkyl group in commercially available column carriers. Alternatively, when biotin is bound to the amino group, the linker can be held on commercially available avidin columns. Thus, when used as $R^2$, a compound having an amino group enables immobilization on a column carrier while maintaining high blocker activity. Alternatively, when the linker is bound to a fluorescent group or fluorescently-labeled avidin instead of a column carrier, this allows detection by fluorescence. Examples of such a linker include amino acids (e.g., β-alanine, 6-aminohexanoic acid), peptides prepared by condensing 2 to 5 of these amino acids, polyethylene glycol derivatives having an amino group and carboxylic acid at both ends, or compounds prepared by condensing the derivatives. Moreover, compounds having an optionally substituted linear or branched $C_1$-$C_{30}$ aliphatic group or an optionally substituted aromatic group as substituent $R^2$ also retain high activity, and allow ligand detection when a radioisotope is partially introduced into the compounds.

The compound of the present invention may be converted into a salt form in a routine manner. Examples of such a salt include alkali metal salts (e.g., sodium salt, potassium salt), alkaline earth metal salts (e.g., calcium salt) and ammonium salt, all of which fall within the present invention. On the other hand, the compound of the present invention may also be converted into a salt form by the action of an ordinary acid. Examples of such a salt include inorganic acid salts (e.g., hydrochloride salt, sulfate salt) and organic acid salts (e.g., acetate salt, citrate salt, trifluoroacetate salt), all of which fall within the present invention.

Method for Preparing Compound of Chemical Formula (1)

Figure 1:
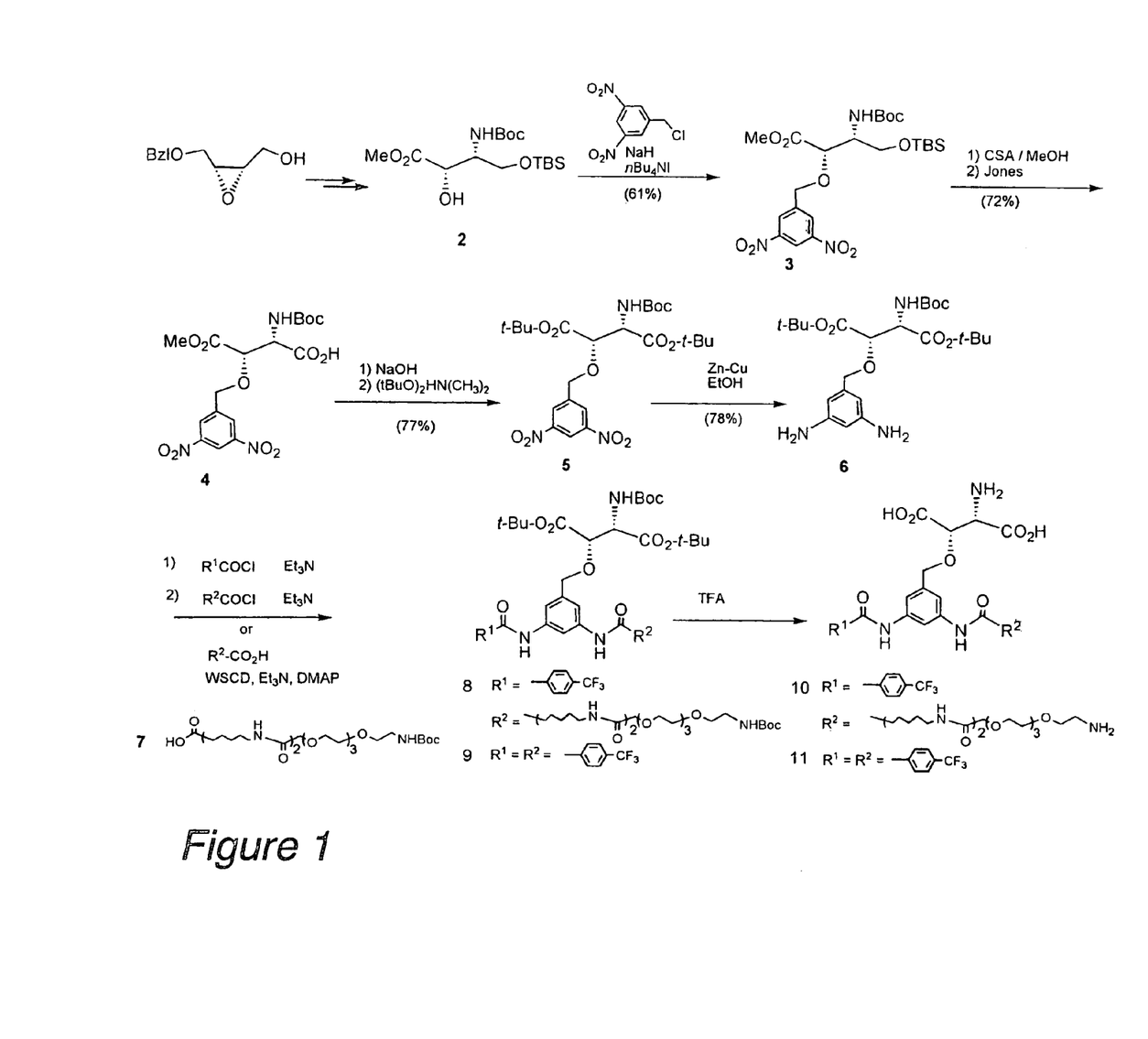
FIG. 1 shows a synthesis scheme for the compound of the present invention (Compounds 10 and 11).

The compound of the present invention can be synthesized according to the scheme shown in FIG. 1.

In FIG. 1, the Boc group represents a tert-butoxycarbonyl group, and TBS represents a t-butyldimethylsilyl group.

Known Compound 2 (Compound 6 in PCT/JP02/06286) derived from an optically active epoxide is treated with 3,5-dinitrobenzyl chloride and sodium hydride to convert its hydroxyl group into dinitrobenzyl ether. After removing the TBS group, the hydroxyl group is oxidized into carboxylic acid. Subsequently, the methyl ester is removed to give free carboxylic acid. These two carboxylic acids are each derived into t-butyl ester. After reducing the nitro groups, only 1 equivalent of carboxylic acid chloride corresponding to $R^1CO$ is added to the resulting amino groups, followed by addition of carboxylic acid chloride or carboxylic acid corresponding to $R^2CO$ together with a condensing agent to give a disubstituted product. All protecting groups are removed by use of a strong acid to obtain the desired compound.

Usefulness of Compound of the Present Invention

The compound of the present invention inhibits intracellular uptake of $^{14}C$-labeled glutamate in human EAAT2 and EAAT3 which are constitutively expressed in MDCK (Madin-Darby Canine Kidney) cells or transiently expressed in COS-1 cells. This indicates that the compound of the present invention is a useful molecular probe involved in elucidating the mechanism of glutamate transporters, and is a useful compound leading to treatment of neurodegenerative diseases through studies on structure-activity relationship studies and/or protein structure analysis.

Among compounds of Formula (1), those having a free amino group can be used as affinity column ligands for use in isolation and purification of glutamate transporter proteins. Affinity columns may be prepared in a known manner (for details of coupling reaction in general, see Affinity Chromatography Handbook Principle and Methods, published by Amersham Pharmacia Biotech). Moreover, when such a compound is reacted with an active ester-containing biotin derivative or fluorescent dye derivative instead of a column carrier, this allows biotin labeling or fluorescence labeling.

Some compounds of Formula (1) are also useful as radioisotope-labeled ligands for use in identification of transporter proteins. For example, in FIG. 2, it is possible to perform hydrogenation after introduction of an unsaturated fatty acid acyl group (e.g., an acryloyl group) as $R^2CO$. In this case, the use of a tritium gas allows isotopic labeling with tritium. Alternatively, as shown in FIG. 3, after introduction of a halogenated benzoyl group as $R^2CO$, the compound is derived into a tin derivative in a known manner and further substituted with [$^{125}I$]NaI, whereby the compound can be labeled with radioactive iodo.

EXAMPLES

The present invention will now be described in more detail by way of the following examples, which are not intended to limit the scope of the invention.

Example 1

Synthesis of (2S,3S)-3-(3-(6-(6-(2-(2-(2-(2-(2-aminoethoxy)ethoxy)ethoxy)ethoxy)acetamido)hexanamido)hexanamido)-5-(4-(trifluoromethyl)benzamido)benzyloxy)aspartic acid (Compound 10 in FIG. 1)

[Formula 4]

Example 1-1

Synthesis of Compound 3 ((2S,3R)-methyl 2-(3,5-dinitrobenzyloxy)-3-(tert-butoxycarbonyl)-4-(tert-butyldimethylsilyloxy)-butanoate) from Compound 2 in FIG. 1

To a solution of Compound 2 (500 mg, 1.38 mmol) in DMF (5 mL), sodium hydride (83 mg, 2.07 mmol) and tetrabutylammonium iodide (152 mg, 0.41 mmol) were added at 0° C. and 3,5-dinitrobenzyl chloride (450 mg, 2.07 mmol) was further added slowly, followed by stirring at room temperature for 30 minutes. Additional sodium hydride and 3,5-dinitrobenzyl chloride (150 mg, 0.70 mmol) were added and stirred at room temperature for 30 minutes. After addition of a 5% aqueous citric acid solution to stop the reaction, the reaction mixture was extracted with ether and the organic layer was dried over magnesium sulfate. The solvent was distilled off and the resulting residue was purified by silica gel column chromatography (ether/hexane=1/3, chloroform/methanol=300/1) to give the titled compound (455 mg, 61%).

Oil; $[\alpha]_D$ +0.85° (c 1.28, CHCl$_3$); $^1$H-NMR (CDCl$_3$, 400 MHz) δ0.05 (s, 3H), 0.08 (s, 3H), 0.86 (s, 9H), 1.42 (s, 9H), 3.59 (t, 1H, J=9.5 Hz), 3.74 (dd, 1H, J=5.5 Hz), 3.79 (s, 3H), 4.23 (m, 1H), 4.44 (d, 1H, J=2.0 Hz), 4.61 (d, 1H, J=12.5 Hz), 4.84 (d, 1H, J=10.0 Hz), 4.97 (d, 1H, J=12.5 Hz), 8.57 (d, 2H, J=2.0 Hz), 8.99 (t, 1H, J=4.0 Hz).

Example 1-2

Synthesis of Compound 5 (di-tert-butyl ester of (2S, 3S)—N(tert-butoxycarbonyl)-3-(3,5-dinitrobenzyloxy)aspartic acid) from Compound 3 in FIG. 1

To a solution of Compound 3 (455 mg, 0.84 mmol) in methanol (3 mL), a catalytic amount of DL-camphorsulfonic acid was added and stirred at room temperature for 18 hours. After addition of saturated aqueous sodium bicarbonate to stop the reaction, the reaction mixture was extracted with ether and the organic layer was washed with saturated aqueous sodium chloride. After the organic layer was dried over magnesium sulfate, the solvent was distilled off and the resulting residue was dissolved in acetone (5 mL), followed by addition of Jones reagent until brown did not disappear. After stirring at room temperature for 30 minutes, 2-propanol was added to stop the reaction. The reaction mixture was extracted with ether and the organic layer was washed with saturated aqueous sodium chloride. The organic layer was dried over magnesium sulfate and the solvent was distilled off to give carboxylic acid (4) (268 mg, 72% for 2 steps). The thus obtained 4 was dissolved in methanol (2 mL) and 1 N NaOH (2.5 mL) was added thereto under ice cooling, followed by stirring at room temperature for 4 hours. The reaction mixture was adjusted with 2 N hydrochloric acid to pH 1 and extracted with ethyl acetate. The solvent was distilled off and the resulting residue was dissolved in N,N-dimethylformamide di-tert-butylacetal (5 mL) and heated at 90° C. for 15 minutes. The reaction mixture was cooled on ice and water was added thereto, followed by stirring for 18 hours. After extraction with ether, the organic layer was washed with saturated aqueous sodium chloride and dried over magnesium sulfate. The solvent was distilled off and the resulting residue was purified by silica gel column chromatography (ether/hexane=1/3) to give the titled compound (257 mg, 77% for 2 steps).

Oil; $[\alpha]_D$ −4.2° (c 1.22, CHCl$_3$); $^1$H-NMR (CDCl$_3$, 400 MHz) δ1.39 (s, 9H), 1.44 (s, 9H), 1.47 (s, 9H), 4.51 (d, 1H, J=2.5 Hz), 4.58 (d, 1H, J=12.5 Hz), 4.81 (dd, 1H, J=2.0, 10.5 Hz), 5.03 (d, 1H, J=12.5 Hz), 5.19 (d, 1H, J=10.5 Hz), 8.50 (d, 2H, J=2.0 Hz), 8.93 (t, 1H, J=2.0 Hz).

Example 1-3

Synthesis of Compound 6 (di-tert-butyl ester of (2S, 3S)—N(tert-butoxycarbonyl)-3-(3,5-diaminobenzyloxy)aspartic acid) from Compound 5 in FIG. 1

Compound 5 (257 mg, 0.47 mmol) was dissolved in ethanol (3 mL). To this solution, active zinc (3.0 g) prepared from zinc powder and a 2% aqueous copper sulfate solution was added and stirred at 80° C. for 18 hours. After cooling and filtration, the filtrate was concentrated. The resulting residue was dissolved in ethyl acetate, washed with saturated aqueous sodium chloride, and then dried over magnesium sulfate. The solvent was distilled off and the resulting residue was purified by silica gel column chromatography (ether/hexane=2/1 to 3/1) to give the titled compound (178 mg, 78%).

Oil; $[\alpha]_D$ −12.5° (c 1.02, CHCl$_3$); $^1$H-NMR (CDCl$_3$, 400 MHz) δ 1.41 (s, 9H), 1.44 (s, 9H), 1.48 (s, 9H), 3.45 (bs, 2H), 4.22 (d, 1H, J=11.0 Hz), 4.40 (d, 1H, J=2.0 Hz), 4.59 (d, 1H, J=11.0 Hz), 4.71 (dd, 1H, J=2.0, 10.5 Hz), 5.28 (d, 1H, J=10.5 Hz), 5.95 (t, 1H, J=1.5 Hz), 6.06 (d, 2H, J=1.5 Hz).

Example 1-4

Synthesis of Compound 8 (di-tert-butyl ester of (2S, 3S)—N-tert-butoxycarbonyl-3-(3-(6-(6-(2-(2-(2-(2-N-tert-butoxycarbonylaminoethoxy)ethoxy)ethoxy)ethoxy)acetamido) hexanamido) hexanamido)-5-(4-(trifluoromethyl)benzamido) benzyloxy)aspartic acid) from Compound 6 in FIG. 1

Compound 6 (120 mg, 0.25 mmol) and triethylamine (104 μL, 0.75 mmol) were dissolved in methylene chloride (5 mL). To this solution, a solution of 4-(trifluoromethyl)benzoyl chloride (37 μL) in methylene chloride (2 mL) was added slowly under ice cooling. After stirring for 15 minutes under ice cooling, a linker (7 in FIG. 1) (288 mg, 0.50 mmol), 1-ethyl-3-(3-dimethylaminopropyl)carbodiimide hydrochloride (96 mg, 0.50 mmol) and 4-N,N-dimethylaminopyridine (30 mg, 0.25 mmol) were added. The reaction mixture was stirred at 40° C. for 2 hours, followed by addition of ether and a 5% aqueous citric acid solution to stop the reaction. The organic layer was washed successively with saturated aqueous sodium chloride, saturated aqueous sodium bicarbonate and saturated aqueous sodium chloride, and then dried over magnesium sulfate. The solvent was distilled off and the resulting residue was purified by silica gel column chromatography (methanol/chloroform=3/97 to 5/95) to give the titled compound (184 mg, 61% for 2 steps) and Compound 9 in FIG. 1 (40 mg, 19%).

Compound 8 oil; $[\alpha]_D$ +4.00 (c 0.93, CHCl$_3$); $^1$H-NMR (CDCl$_3$, 400 MHz) δ 1.25-1.55 (m, 8H), 1.42 (s, 27H), 1.48 (s, 9H), 1.60 (tt, 2H, J=7.5 Hz), 1.71 (tt, 2H, J=7.5 Hz), 2.15 (t, 2H, J=7.0 Hz), 2.36 (t, 2H, J=7.0 Hz), 3.25 (m, 6H), 3.50 (m, 2H), 3.55-3.70 (m, 14H), 3.96 (d, 2H, J=5.0 Hz), 3.99 (d, 1H, J=11.5 Hz), 4.43 (s, 1H), 4.76 (d, 2H, J=11.5 Hz), 5.10 (bs, 1H), 5.35 (d, 1H, J=10.5 Hz), 5.95 (bs, 1H), 7.05 (bs, 1H), 7.31 (s, 1H), 7.45 (s, 1H), 7.73 (d, 2H, J=8.0 Hz), 7.99 (s, 1H), 8.01 (d, 2H, J=8.0 Hz), 8.24 (bs, 1H), 8.60 (bs, 1H).

Compound 9 oil; $[\alpha]_D$ +3.5° (c 1.34, CHCl$_3$); $^1$H-NMR (CDCl$_3$, 400 MHz) δ 1.41 (s, 18H), 1.49 (s, 9H), 4.44 (d, 1H, J=12.0 Hz), 4.46 (d, 1H, J=2.5 Hz), 4.80 (dd, 1H, J=2.5, 10.5 Hz), 5.37 (d, 1H, J=10.5 Hz), 7.46 (d, 2H, J=1.5 Hz), 7.72 (d, 4H, J=8.0 Hz), 7.95 (d, 4H, J=8.0 Hz), 8.19 (s, 1H), 8.31 (s, 2H).

Example 1-5

Synthesis of Compound 10 ((2S,3S)-3-(3-(6-(6-(2-(2-(2-(2-(2-aminoethoxy)ethoxy)ethoxy)ethoxy)acetamido)hexanamido) hexanamido)-5-(4-(trifluoromethyl)benzamido)benzyloxy) aspartic acid) from Compound 8 in FIG. 1

Compound 8 (184 mg, 0.15 mmol) was dissolved in chloroform (1 mL) and trifluoroacetic acid (TFA; 1 mL) was added thereto, followed by stirring at room temperature for 18 hours. The solvent was distilled off and the resulting residue was co-evaporated with chloroform. This procedure was repeated three times. The residue was dissolved in water and lyophilized twice to give the titled compound as a TFA salt (104 mg, 62%).

Amorphous; $[\alpha]_D$ −19.1° (c 0.37, $H_2O$); $^1$H-NMR ($D_2O$, 400 MHz) δ 1.05 (m, 2H), 1.15 (m, 2H), 1.26 (m, 2H), 1.32 (m, 4H), 1.44 (m, 2H), 1.98 (t, 2H, J=7.8 Hz), 2.16 (m, 2H), 2.96 (t, 4H, J=7.0 Hz), 3.05 (m, 2H), 3.46-3.64 (m, 16H), 3.83 (s, 2H), 4.30 (d, 1H, J=12 Hz), 4.36 (d, 1H, J=2.5 Hz), 4.50 (d, 1H, J=2.5 Hz), 4.54 (d, 1H, J=12 Hz), 7.00 (s, 1H), 7.09 (s, 1H), 7.49 (d, 2H, J=8.5 Hz), 7.60 (s, 1H), 7.68 (d, 2H, J=8.5 Hz).

Example 1-6

Synthesis of Compound 11 ((2S,3S)-3-{3,5-bis[4-(trifluoromethyl)benzamido]benzyloxy}aspartic acid) from Compound 9 in FIG. 1

Compound (9) (27 mg, 0.033 mmol) was dissolved in chloroform (1 mL) and trifluoroacetic acid (TFA; 1 mL) was added thereto, followed by stirring at room temperature for 18 hours. The solvent was distilled off and the resulting residue was co-evaporated with chloroform. This procedure was repeated three times. The residue was dissolved in water and lyophilized twice to give the titled compound as a TFA salt (20 mg, 84%).

Amorphous; $^1$H-NMR ($D_2O$, 400 MHz) δ 4.01 (d, 1H, J=5.0 Hz), 4.41 (d, 1H, J=5.0 Hz), 4.49 (d, 1H, J=11.0 Hz), 4.74 (d, 1H, J=11.0 Hz), 7.48 (s, 2H), 7.88 (d, 4H, J=8.0 Hz), 8.10 (d, 4H, J=8.0 Hz), 8.21 (d, 1H, J=1.5 Hz).

Example 2

Figure 2:
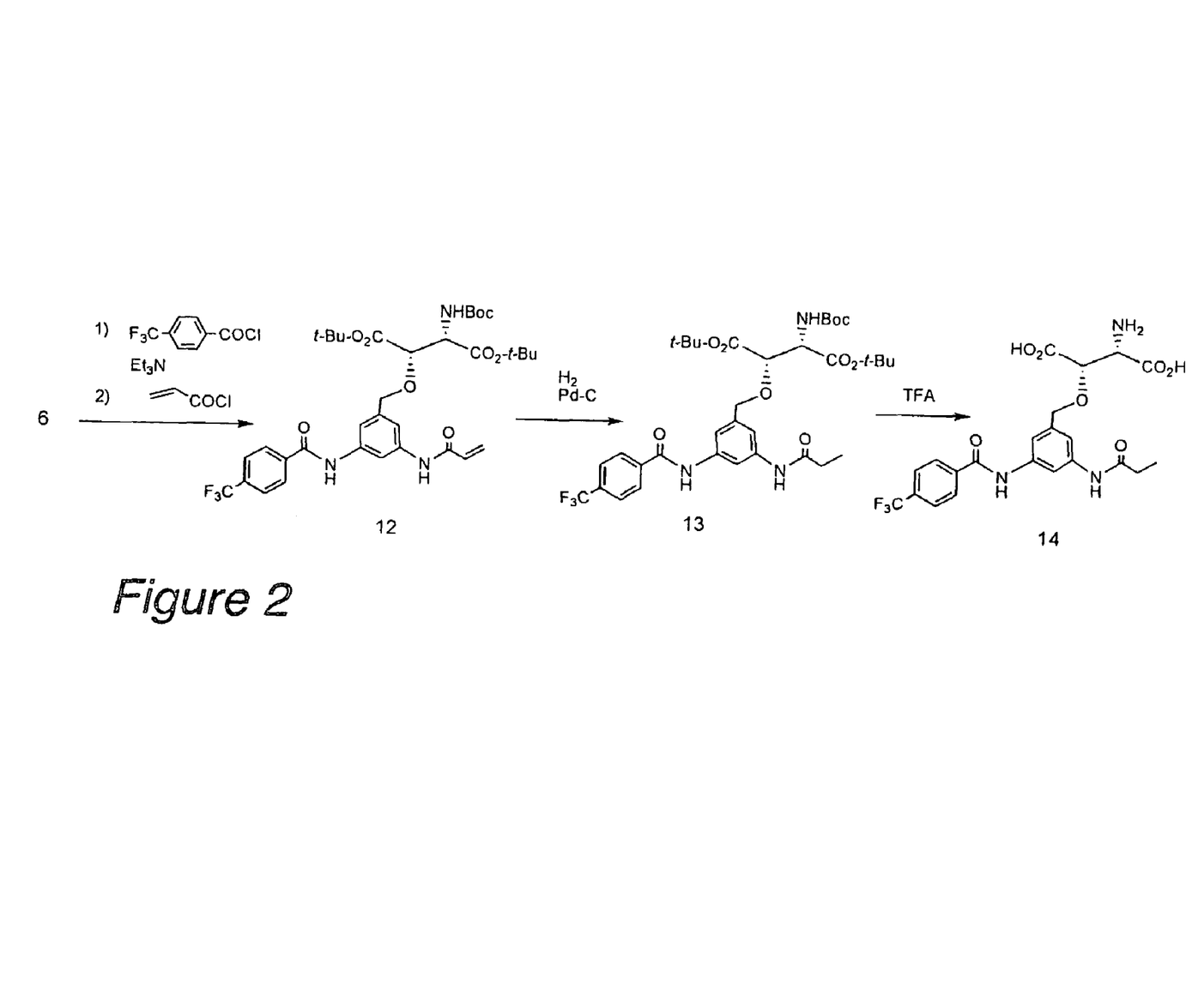
FIG. 2 shows a synthesis scheme for the compound of the present invention (Compound 14).
Figure 3:
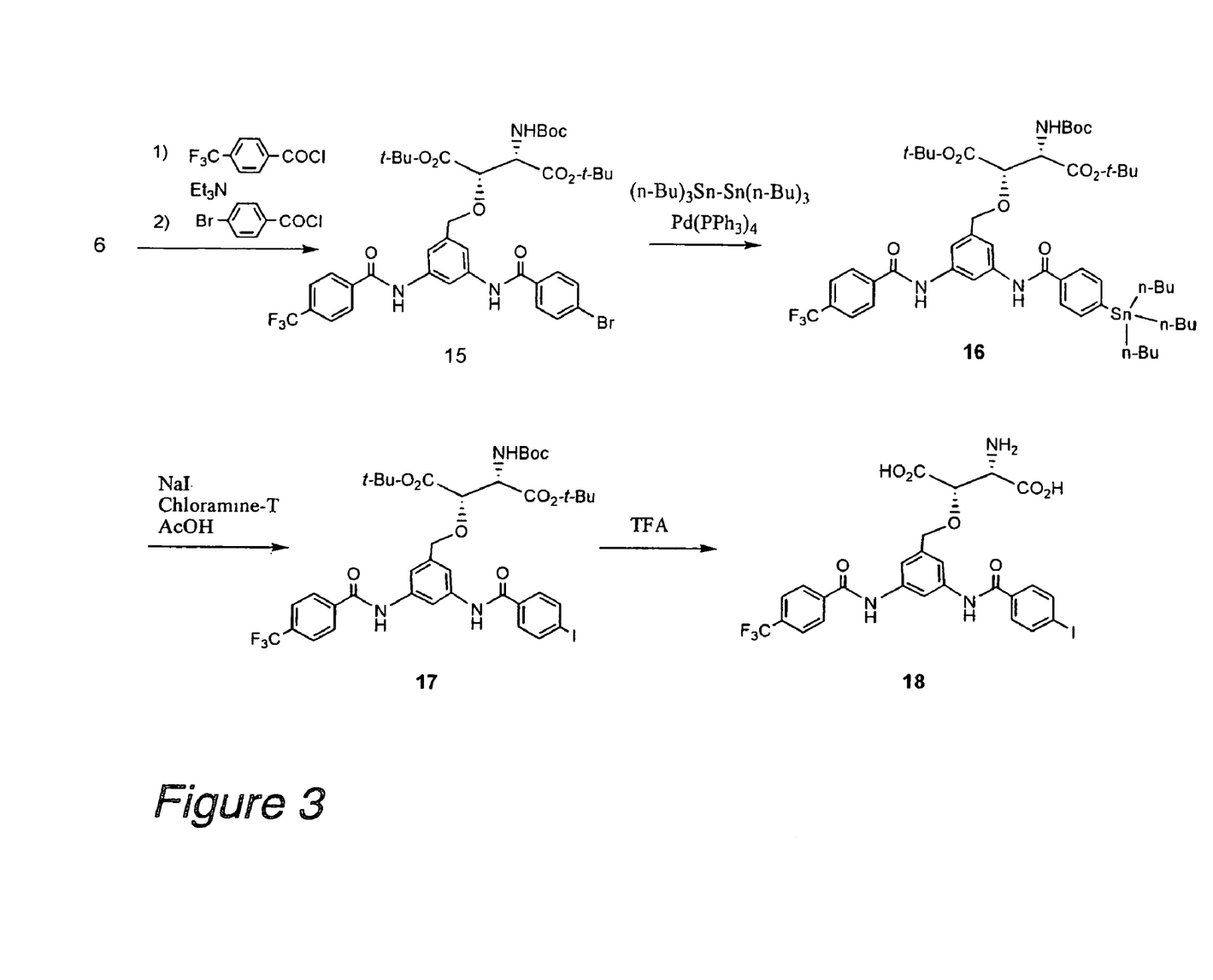
FIG. 3 shows a synthesis scheme for the compound of the present invention (Compound 18).

Synthesis of (2S,3S)-3-(3-propionylamido-5-[4-(trifluoromethyl)benzamido]benzyloxy)aspartic acid (Compound 14 in FIG. 2)

[Formula 5]

Example 2-1

Synthesis of Compound 12 in FIG. 2 (di-tert-butyl ester of (2S,3S)—N-tert-butoxycarbonyl-3-{3-acrylamido-5-[4-(trifluoromethyl)benzamido]benzyloxy}aspartic acid) from Compound 6 in FIG. 1

Compound 6 (20 mg, 0.042 mmol) and triethylamine (17 μL, 0.13 mmol) were dissolved in methylene chloride (5 mL). To this solution, a solution of trifluoromethylbenzoyl chloride (6.7 μL, 0.042 mmol) in methylene chloride (2 mL) was added slowly under ice cooling. After stirring for 15 minutes under ice cooling, acryloyl chloride (4.0 μL, 0.050 mmol) was added. The reaction mixture was stirred for an additional 15 minutes, followed by addition of ether and saturated aqueous sodium bicarbonate to stop the reaction. The organic layer was washed successively with saturated aqueous sodium chloride, a 5% aqueous citric acid solution and saturated aqueous sodium chloride, and then dried over magnesium sulfate. The solvent was distilled off and the resulting residue was purified by silica gel column chromatography (ether/hexane=1/3) to give the titled compound (18.7 mg, 63% for 2 steps).

Oil; $^1$H-NMR ($CDCl_3$, 400 MHz) δ 1.41 (s, 18H), 1.49 (s, 9H), 4.41 (d, 1H, J=11.5 Hz), 4.45 (d, 1H, J=2.5 Hz), 4.79 (d, 2H, J=11.0 Hz), 5.38 (d, 1H, J=10.5 Hz), 5.76 (dd, 1H, J=1.0, 10.5 Hz), 6.25 (dd, 1H, J=10.5, 16.5 Hz), 6.40 (dd, 1H, J=1.0, 16.5 Hz), 7.33 (s, 1H), 7.46 (s, 1H), 7.74 (d, 2H, J=8.0 Hz), 7.75 (s, 1H), 7.96 (d, 2H, J=8.0 Hz), 8.03 (s, 1H), 8.24 (s, 1H).

Example 2-2

Synthesis of Compound 13 (di-tert-butyl ester of (2S,3S)—N-tert-butoxycarbonyl-3-{3-propionylamido-5-[4-(trifluoromethyl)benzamido]benzyloxy}-aspartic acid) from Compound 12 in FIG. 2

Compound 12 (18 mg, 0.025 mmol) was dissolved in methanol (2 mL) and 10% palladium carbon was added thereto, followed by stirring for 2 hours under a hydrogen atmosphere. The catalyst was filtered off and the filtrate was concentrated to give the titled compound (16.0 mg, 89%).

Oil; $^1$H-NMR ($CDCl_3$, 400 MHz) δ 1.23 (t, 3H, J=7.5 Hz), 1.42 (s, 9H), 1.43 (s, 9H), 1.49 (s, 9H), 2.37 (q, 2H, J=7.5 Hz), 4.40 (d, 1H, J=11.5 Hz), 4.45 (d, 1H, J=2.5 Hz), 4.77 (d, 1H, J=10.0 Hz), 4.78 (dd, 1H, J=2.5, 10.0 Hz), 5.37 (d, 1H, J=10.0 Hz), 7.37 (s, 1H), 7.44 (s, 1H), 7.66 (d, 2H, J=8.0 Hz), 7.90 (d, 2H, J=8.0 Hz), 7.81 (s 1H), 8.13 (s, 1H).

Example 2-3

Synthesis of Compound 14 ((2S,3S)-3-{3-propionylamido-5-[4-(trifluoromethyl)benzamido]benzyloxy}aspartic acid) from Compound 13 in FIG. 2

Compound 13 (16.0 mg, 0.023 mmol) was dissolved in chloroform (1 mL) and TFA (1 mL) was added thereto, followed by stirring at room temperature for 18 hours. The solvent was distilled off and the resulting residue was co-evaporated with chloroform. This procedure was repeated three times. The residue was suspended in water and lyophilized twice to give the titled compound as a TFA salt (13.6 mg, 98%).

Amorphous; $^1$H-NMR ($D_2O$, 400 MHz) δ 1.05 (t, 3H, J=7.5 Hz), 2.29 (q, 2H, J=7.5 Hz), 4.04 (d, 1H, J=3.0 Hz), 4.41 (d, 1H, J=3.0 Hz), 4.43 (d, 1H, J=11.5 Hz), 4.67 (d, 1H, J=11.5 Hz), 7.29 (s, 1H), 7.35 (s, 1H), 7.85 (d, 2H, J=8.0 Hz), 7.99 (s, 1H), 8.06 (d, 2H, J=8.0 Hz).

Example 3

Assay of Biological Activity

Measurement of Glutamate Transporter Inhibitory Activity

According to the known method (Shimamoto, K. et al., Mol. Pharmacol. 53, 195-201, 1998; Bioorg. Med. Chem. Lett. 10, 2407-2410, 2000), the inhibitory effect against [$^{14}$C] glutamate uptake was measured in human EAAT2 or EAAT3 constitutively expressed in MDCK (Madin-Darby Canine Kidney) cells. Glutamate uptake activity was determined as follows: 1 μM L-[$^{14}$C]glutamate and a sample at a given concentration were added and incubated for 12 minutes, followed by solubilizing the cells to measure incorporated radioactivity with a liquid scintillator. The amount of uptake was expressed as a percentage, assuming that uptake in the absence of a test compound (buffer alone) was set to 100% and uptake in a sodium-free solution was set to 0%. $IC_{50}$ values were determined and shown in Table 1.

[Table 1]

TABLE 1

Glutamate uptake inhibition by disubstituted analogs and control compounds

|  | EAAT2 $IC_{50}$ (nM) | EAAT3 $IC_{50}$ (nM) |
| --- | --- | --- |
| L-TBOA | 1300 | 1300 |
| TFB-TBOA | 1.9 | 28 |
| Compound 10 | 23 | 805 |
| Compound 11 | 1.3 | 0.46 |
| Compound 14 | 4.7 | 112 |

Example 4

Binding to Column

Preparation Example 1

A given amount of Affi-Gel 10 or Affi-Gel 15 (BioRad) is weighed on a glass filter and washed successively with ice-cold anhydrous 2-propanol and the reaction solvent (alcohol, dimethylsulfide (DMSO), dioxane, formamide). A ligand falling within the present invention is dissolved in the reaction solvent and adjusted to pH 10-11 by addition of a tertiary amine (e.g., triethylamine, diisopropylethylamine). The swollen gel and the ligand solution are mixed together and reacted at room-temperature for several hours. Excess ligand is washed off. The gel is stored at 4° C.

Preparation Example 2

A given amount of CNBr-activated Sepharose 4B (Amersham Bioscience) is weighed on a glass filter. 1 mM HCl is used to repeat washing and swelling. The ligand of the present invention is dissolved in coupling buffer (e.g., 0.1 M $NaHCO_3$ (pH 8.3) containing 0.5 M NaCl). This ligand is mixed with the gel dispersion at room temperature for 2 hours or overnight at 4° C. Next, the gel is introduced into a blocking agent (e.g., 1 M ethanolamine or 0.2 M glycine, pH 8.0). This gel is washed with coupling buffer and acetate buffer (0.5 M NaCl, 0.1 M AcOH, pH 4.0) to remove excess ligand and blocking agent. The gel is stored at 4° C.

INDUSTRIAL APPLICABILITY

According to the present invention, a derivative represented by chemical formula (1) or a salt thereof, which has two amino groups on the benzene ring of optically active β-benzyloxyaspartic acid, can be provided as a ligand for affinity columns or as a ligand for protein detection.

The invention claimed is:

1. A compound of Formula (1) or a salt thereof:

[Formula 6]

wherein $R^1$ represents an optionally substituted aromatic group; and substituent $R^2$ represents a group selected from an optionally substituted linear or branched $C_1$-$C_{30}$ aliphatic group whose chain may contain nitrogen or oxygen, and an optionally substituted aromatic group.

2. The compound according to claim 1, wherein the substituent $R^2$ is substituted with an amino group at its end.

3. The compound according to claim 1, wherein the substituent $R^2$ is an aliphatic group having an oxygen atom and a nitrogen atom within its chain.

4. The compound according to claim 1, wherein the compound of Formula (1) is (2S,3S)-3-(3-(6-(6-(2-(2-(2-(2-(2-aminoethoxy)ethoxy)ethoxy)ethoxy)acetamido)hexanamido)hexanamido)-5-(4-(trifluoromethyl)benzamido)benzyloxy)aspartic acid.

5. An affinity column ligand comprising the compound according to claim 1.

6. An affinity column ligand comprising the compound according to claim 4.

7. A ligand for fluorescence detection, comprising the compound according to claim 1.

8. A ligand for fluorescence detection, comprising the compound according to claim 4.

9. A method for purifying a L-glutamate transporter protein in a biological sample, which comprises the steps of:

preparing an affinity column by using the compound according to claim 2 as an affinity column ligand having a free amino group and allowing the compound to bind to a column carrier reactive with a free amino group;

contacting a biological sample likely to contain a L-glutamate transporter protein with the affinity column;

washing the affinity column; and eluting the L-glutamate transporter protein from the affinity column.

10. The method according to claim 9, wherein the compound of Formula (1) (2S,3S)-3-(3-(6-(6-(2-(2-(242-(2-aminoethoxy)ethoxy)ethoxy)ethoxy)acetamido)hexanamido)hexanamido)-5-(4-(trifluoromethyl)benzamido)benzyloxy)aspartic acid is used as an affinity column ligand.

11. A method for purifying a L-glutamate transporter protein in a biological sample, which comprises the steps of:
preparing a column by allowing the compound having a free amino group according to claim 2 to bind to biotin and then holding the resulting bound product on an avidin column;
contacting a biological sample likely to contain a L-glutamate transporter protein with the column;
washing the column; and
eluting the L-glutamate transporter protein from the column.

12. The method according to claim 11, wherein the compound of Formula (1) (2S,3S)-3-(3-(646-(2-(2-(2-(2-(2-aminoethoxy)ethoxy)ethoxy)acetamido)hexanamido)hexanamido)-5-(4-(trifluoromethyl)benzamido)benzyloxy)aspartic acid is used as a column ligand.

13. A fluorescence-based method for detecting a L-glutamate transporter protein, which comprises the steps of:
allowing the compound according to claim 1 to bind to biotin, and then allowing the resulting bound product to bind to a fluorescent group or fluorescently-labeled avidin;
contacting a biological sample likely to contain a L-glutamate transporter protein with the bound product; and
fluorescently detecting the presence or absence of binding with the biotin-avidin bound product in the sample.

14. The method according to claim 13, wherein the compound of Formula (1) (2S,3S)-3-(3-(6-(6-(2-(2-(2-(2-(2-aminoethoxy)ethoxy)ethoxy)ethoxy)acetamido)hexanamido)hexanamido)-5-(4-(trifluoromethyl)benzamido)benzyloxy)aspartic acid is used.

* * * * *